(12) United States Patent
Bennison et al.

(10) Patent No.: US 12,023,470 B2
(45) Date of Patent: Jul. 2, 2024

(54) SYSTEM FOR CONTROLLING GAS GENERATION WITHIN A DRUG DELIVERY DEVICE

(71) Applicant: Eli Lilly and Company, Indianapolis, IN (US)

(72) Inventors: Corrie Jo Bennison, Lewis Center, OH (US); Anthony David Duong, Columbus, OH (US); Jeffrey Leclair Ellis, Columbus, OH (US); Michael W. Harrison, Sharon, MA (US); Lampros C. Kourtis, Cambridge, MA (US); Rhea Sirkar, Brighton, MA (US); John Paul Tallarico, Powell, OH (US)

(73) Assignee: Eli Lilly and Company, Indianapolis, IN (US)

( * ) Notice: Subject to any disclaimer, the term of this patent is extended or adjusted under 35 U.S.C. 154(b) by 80 days.

(21) Appl. No.: 16/645,320

(22) PCT Filed: Aug. 31, 2018

(86) PCT No.: PCT/US2018/049048
§ 371 (c)(1),
(2) Date: Mar. 6, 2020

(87) PCT Pub. No.: WO2019/050791
PCT Pub. Date: Mar. 14, 2019

(65) Prior Publication Data
US 2021/0038816 A1 Feb. 11, 2021

Related U.S. Application Data

(60) Provisional application No. 62/555,808, filed on Sep. 8, 2017.

(51) Int. Cl.
*A61M 5/20* (2006.01)
*A61M 5/19* (2006.01)

(52) U.S. Cl.
CPC ............ *A61M 5/2046* (2013.01); *A61M 5/19* (2013.01)

(58) Field of Classification Search
CPC ...... A61M 2005/14204; A61M 5/2046; A61M 5/155; A61M 2205/8231; B65D 83/643
See application file for complete search history.

(56) References Cited

U.S. PATENT DOCUMENTS

| 2,390,246 A | 12/1945 | Folkman |
| 2,446,429 A | 8/1948 | Nelson et al. |
| (Continued) | | |

FOREIGN PATENT DOCUMENTS

| DE | 3809482 | 10/1989 |
| EP | 2221076 | 8/2010 |
| (Continued) | | |

OTHER PUBLICATIONS

International Search Report of the International Searching Authority pertaining to International Application No. PCT/US2018/049048; dated Nov. 27, 2018; 6 pages.
(Continued)

*Primary Examiner* — Emily L Schmidt
(74) *Attorney, Agent, or Firm* — Jonathan C. Anderson (57) ABSTRACT

A chemical reaction system is disclosed for use in a device for delivering a therapeutic fluid comprising a liquid base and a polymeric acid. A reaction rate of the chemical reaction system is capable of being adjusted by adjusting at least one of surface area-to-volume ratio, acid concentration, and cross-linking of the polymeric acid.

15 Claims, 12 Drawing Sheets

(56) References Cited

U.S. PATENT DOCUMENTS

| | | | |
|---|---|---|---|
| 2,833,745 A | 5/1958 | Filkentscher | |
| 2,923,243 A | 2/1960 | Crockford et al. | |
| 3,405,845 A | 10/1968 | Cook et al. | |
| 3,467,526 A | 9/1969 | Mitchell et al. | |
| 3,556,803 A | 1/1971 | Ehrreich, III et al. | |
| 3,594,410 A | 7/1971 | Cohen et al. | |
| 3,754,993 A | 8/1973 | Oguchi et al. | |
| 3,773,111 A | 11/1973 | Dunn | |
| 3,968,796 A | 7/1976 | Baker | |
| 4,031,889 A | 6/1977 | Pike | |
| 4,203,441 A | 5/1980 | Theeuwes | |
| 4,675,174 A * | 6/1987 | Eckenhoff | A61K 9/0004 424/466 |
| 4,744,786 A | 5/1988 | Hooven | |
| 4,785,972 A | 11/1988 | LeFevre | |
| 4,795,748 A | 1/1989 | Ross et al. | |
| 5,034,114 A | 7/1991 | Kukin | |
| 5,062,834 A | 11/1991 | Gross et al. | |
| 5,151,093 A | 9/1992 | Theeuwes et al. | |
| 5,167,641 A | 12/1992 | Schmitz | |
| 5,279,607 A * | 1/1994 | Schentag | A61B 5/0031 604/890.1 |
| 5,304,128 A | 4/1994 | Haber et al. | |
| 5,312,389 A | 5/1994 | Theeuwes et al. | |
| 5,398,850 A | 3/1995 | Sancoff et al. | |
| 5,518,145 A | 5/1996 | Chen | |
| 5,540,665 A | 7/1996 | Mercado et al. | |
| 5,645,824 A | 7/1997 | Lim et al. | |
| 5,700,245 A | 12/1997 | Sancoff et al. | |
| 5,855,761 A | 1/1999 | Joshi | |
| 5,858,001 A | 1/1999 | Tsals et al. | |
| 5,871,125 A | 2/1999 | Gross | |
| 5,891,087 A | 4/1999 | Ohtani et al. | |
| 5,941,857 A | 8/1999 | Nguyen et al. | |
| 5,992,700 A | 11/1999 | McGlothlin et al. | |
| 6,086,568 A | 7/2000 | Caizza | |
| 6,086,569 A | 7/2000 | Schweizer | |
| 6,156,014 A | 12/2000 | Petersen et al. | |
| 6,270,479 B1 | 8/2001 | Bergens et al. | |
| 6,431,468 B1 | 8/2002 | Brown et al. | |
| 6,575,961 B2 | 6/2003 | Joshi | |
| 6,786,365 B2 | 9/2004 | Kim | |
| 6,830,560 B1 | 12/2004 | Gross et al. | |
| 6,913,593 B1 | 7/2005 | Alexandre et al. | |
| 6,964,356 B2 | 11/2005 | Kim | |
| 7,632,245 B1 | 12/2009 | Cowan et al. | |
| 7,717,877 B2 | 5/2010 | Lavi et al. | |
| 7,753,884 B2 | 7/2010 | Gallnböck | |
| 7,985,309 B2 | 7/2011 | Kim | |
| 7,988,663 B2 | 8/2011 | Schiller et al. | |
| 8,157,769 B2 | 4/2012 | Cabiri | |
| 8,353,426 B2 | 1/2013 | Wold et al. | |
| 8,353,679 B2 | 1/2013 | Yamamoto et al. | |
| 9,321,581 B2 | 4/2016 | Bennison et al. | |
| 2001/0025168 A1 | 9/2001 | Gross et al. | |
| 2001/0050085 A1 | 12/2001 | Knudson et al. | |
| 2002/0156461 A1 | 10/2002 | Joshi | |
| 2003/0168480 A1 | 9/2003 | Kim | |
| 2004/0249339 A1 | 12/2004 | Willis et al. | |
| 2005/0006401 A1 | 1/2005 | Kim | |
| 2005/0187522 A1 | 8/2005 | Miller | |
| 2006/0235264 A1 | 10/2006 | Vassallo | |
| 2007/0088337 A1 | 4/2007 | Lautenbach | |
| 2007/0228071 A1 | 10/2007 | Kamen et al. | |
| 2008/0066766 A1 | 3/2008 | Paraschac et al. | |
| 2008/0069811 A1 * | 3/2008 | Zaidi | A61P 19/08 424/130.1 |
| 2008/0233029 A1 | 9/2008 | Fan et al. | |
| 2008/0257915 A1 | 10/2008 | Wold | |
| 2009/0093787 A1 | 4/2009 | Barbour | |
| 2009/0131860 A1 | 5/2009 | Nielsen | |
| 2009/0227942 A1 | 9/2009 | Stroem Hansen et al. | |
| 2009/0259176 A1 | 10/2009 | Yairi | |
| 2009/0259179 A1 | 10/2009 | Hillios et al. | |
| 2010/0030152 A1 | 2/2010 | Lee et al. | |
| 2010/0069846 A1 | 3/2010 | Stamp | |
| 2010/0137808 A1 | 6/2010 | Wilmot et al. | |
| 2010/0174225 A1 | 7/2010 | Pesach et al. | |
| 2011/0054390 A1 | 3/2011 | Searle et al. | |
| 2011/0092906 A1 | 4/2011 | Bottger et al. | |
| 2011/0270188 A1 | 11/2011 | Caffey et al. | |
| 2011/0272271 A1 | 11/2011 | Hong et al. | |
| 2012/0078216 A1 | 3/2012 | Smith et al. | |
| 2013/0253472 A1 | 9/2013 | Cabiri | |
| 2014/0103075 A1 | 4/2014 | Bennison et al. | |
| 2015/0314070 A1 * | 11/2015 | Heintz | F01B 1/01 222/1 |
| 2016/0156060 A1 | 6/2016 | Hamelers et al. | |
| 2016/0213846 A1 | 7/2016 | Bennison et al. | |
| 2016/0213847 A1 | 7/2016 | Bennison et al. | |
| 2016/0213859 A1 | 7/2016 | Sadowski et al. | |

FOREIGN PATENT DOCUMENTS

| | | |
|---|---|---|
| EP | 2489387 | 8/2012 |
| JP | 2004339496 | 12/2004 |
| WO | 92019571 | 11/1992 |
| WO | 95001198 | 1/1995 |
| WO | 95023641 | 9/1995 |
| WO | 97028750 | 8/1997 |
| WO | 99012593 | 3/1999 |
| WO | 99022790 | 5/1999 |
| WO | 99062576 | 12/1999 |
| WO | 01000270 | 1/2001 |
| WO | 07071485 | 6/2007 |
| WO | 09116045 | 9/2009 |
| WO | 09144726 | 12/2009 |
| WO | 2012122643 | 9/2012 |
| WO | 14059444 | 4/2014 |
| WO | 2015160600 | 10/2015 |
| WO | 2018152018 | 8/2018 |

OTHER PUBLICATIONS

Written Opinion of the International Searching Authority pertaining to International Application No. PCT/US2018/049048; dated Nov. 27, 2018; 8 pages.

"Development of an on-Demand, Generic, Drug-Delivery System," Southern Research Institute, 2000 Ninth Avenue South, Birmingham, AL 35255-5305 Aug. 6, 1985; 30 pages.

Good, Brian T., et al., "An Effervescent Reaction Micropump for Portable Microfluidic Systems," *Lab Chip*, 2006, 6, 659-66; 8 pages.

Jobando, V. O., & Quarles, C. A. Effect of cross-linking on the free volume properties of natural rubber. *physica status solidi c* (2007), 4(10), 3759-3762; 4 pages.

Choudalakis, G., & Gotsis, A. D. Free volume and mass transport in polymer nanocomposites. *Current opinion in colloid & interface science* (2012), 17(3), 132-140; 9 pages.

Ahmed, Enas M. Hydrogel: Preparation, characterization, and applications: a review. *Journal of advanced research* (2015), 6(2), 105-121; 17 pages.

* cited by examiner

SYSTEM FOR CONTROLLING GAS GENERATION WITHIN A DRUG DELIVERY DEVICE

CROSS REFERENCE TO RELATED APPLICATION

This application claims priority to U.S. Provisional Application No. 62/555,808, filed Sep. 8, 2017, the disclosure of which is hereby expressly incorporated by reference herein in its entirety.

FIELD OF THE DISCLOSURE

The present disclosure relates to a system for controlling gas production within drug delivery devices. More particularly, the present disclosure relates to liquid base-polymeric acid chemical reaction systems for controlling gas generation rates for propelling a therapeutic fluid from a drug delivery device.

BACKGROUND OF THE DISCLOSURE

Recently, chemical reaction systems have been used to power the delivery of therapeutic fluids through drug delivery devices. In general, the chemical reaction systems used have included a liquid acid-powder base reaction that generates a gas that in turn is used to propel and deliver the therapeutic fluid from the drug delivery device. However, it has proven difficult to control the rate of these reactions, specifically as needed for the slow delivery of the therapeutic fluid.

As such, it would be desirable to provide reaction systems capable of controlling the rate at which a therapeutic fluid is administered from a drug delivery device, specifically controlling the rate such that the therapeutic fluid is capable of being delivered in a slower manner. These reaction systems may be used to deliver any number of therapeutic fluids, for example, high-concentration proteins, high-viscosity pharmaceutical formulations, or other therapeutic fluids.

SUMMARY

The present disclosure provides a system for controlling the generation of gas within a drug delivery device. More specifically, the present disclosure provides a liquid base-polymeric acid chemical reaction system that is capable of controlling the rate of gas generation within the drug delivery device to control a speed of delivery of a therapeutic fluid from the drug delivery device.

According to an embodiment of the present disclosure, a device is disclosed for delivering a therapeutic fluid by a chemical reaction. The device includes a housing having a first chamber, a second chamber, and a third chamber. The device has a loaded configuration in which the first chamber contains a liquid base, the second chamber contains a polymeric acid, and the third chamber contains the therapeutic fluid, and a delivery configuration in which the liquid base reacts with the polymeric acid and generates a propellant gas that delivers the therapeutic fluid from the third chamber.

According to another embodiment of the present disclosure, a method is disclosed for delivering a therapeutic fluid by a chemical reaction, the method comprising: providing a device containing a liquid base, a polymeric acid, and a therapeutic fluid, the liquid base configured to react with the polymeric acid to generate a propellant gas that delivers the therapeutic fluid from the device.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

The present disclosure provides systems for generating gas used to operate drug delivery devices. These systems include chemical reaction systems comprising liquid base-polymeric acid reactions that can be adjusted to provide controllable gas release, which allows for a range of slower delivery rates of therapeutic fluids from a drug delivery device.

1. THERAPEUTIC FLUIDS

The therapeutic fluid or drug product to be dispensed from the drug delivery devices of the present disclosure may take various forms, such as a solution, dispersion, suspension, emulsion, or another suitable fluid form. The drug delivery devices are operated in a manner generally as described herein by a patient, caregiver or healthcare professional to deliver drug to a person.

The therapeutic fluid may contain a therapeutically useful agent. The therapeutic agent may include insulin, insulin analog such as insulin lispro or insulin glargine, insulin derivative, GLP-1 receptor agonist such as dulaglutide or liraglutide, glucagon, glucagon analog, glucagon derivative, gastric inhibitory polypeptide (GIP), GIP analog, GIP derivative, oxyntomodulin analog, oxyntomodulin derivative, therapeutic antibody and any therapeutic agent that is capable of delivery by the devices of the present disclosure. The therapeutic agent as used in the device may be formulated with one or more excipients.

In certain embodiments, the agent is protein, such as a monoclonal antibody or some other protein which is therapeutically useful. In some embodiments, the protein may have a concentration of from about 75 mg/mL to about 500 mg/mL in the therapeutic fluid. In certain embodiments, the protein may have a concentration of about 150 mg/mL, 200 mg/mL, 250 mg/mL, or more. The therapeutic fluid may further contain a solvent or non-solvent, such as water, perfluoroalkane solvent, safflower oil, or benzyl benzoate.

In some embodiments, the therapeutic fluid may be considered a high-viscosity fluid and may have an absolute viscosity of from about 5 cP to about 1000 cP. In certain embodiments, the high-viscosity fluid has an absolute viscosity of at least about 10 cP, 20 cP, 30 cP, 40 cP, 50 cP, 60 cP, or more.

2. DELIVERY DEVICE WITH CHEMICAL REACTION SYSTEM

Figure 1:
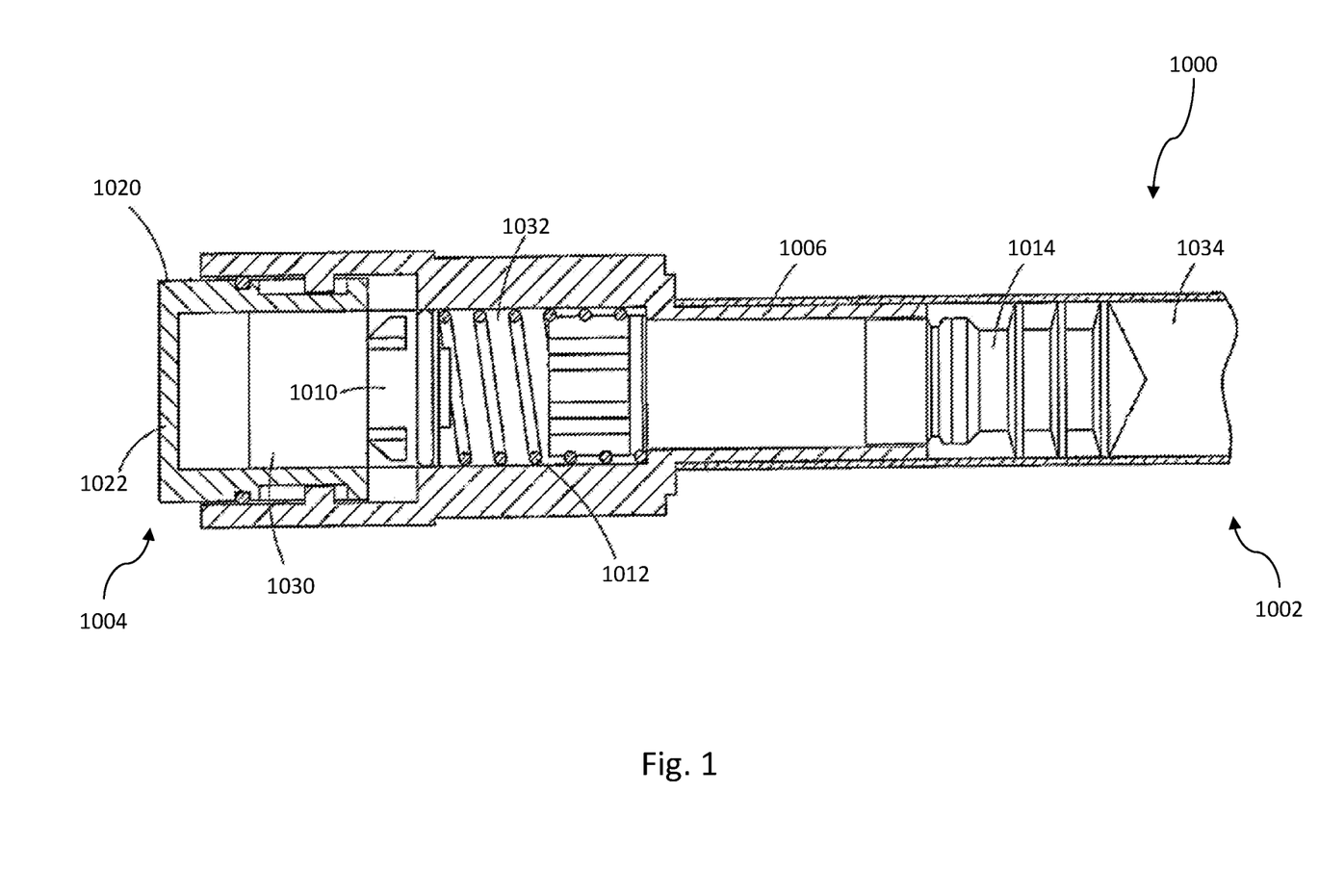
FIG. 1 shows a cross-sectional view of an exemplary delivery device of the present disclosure.
Figure 2:
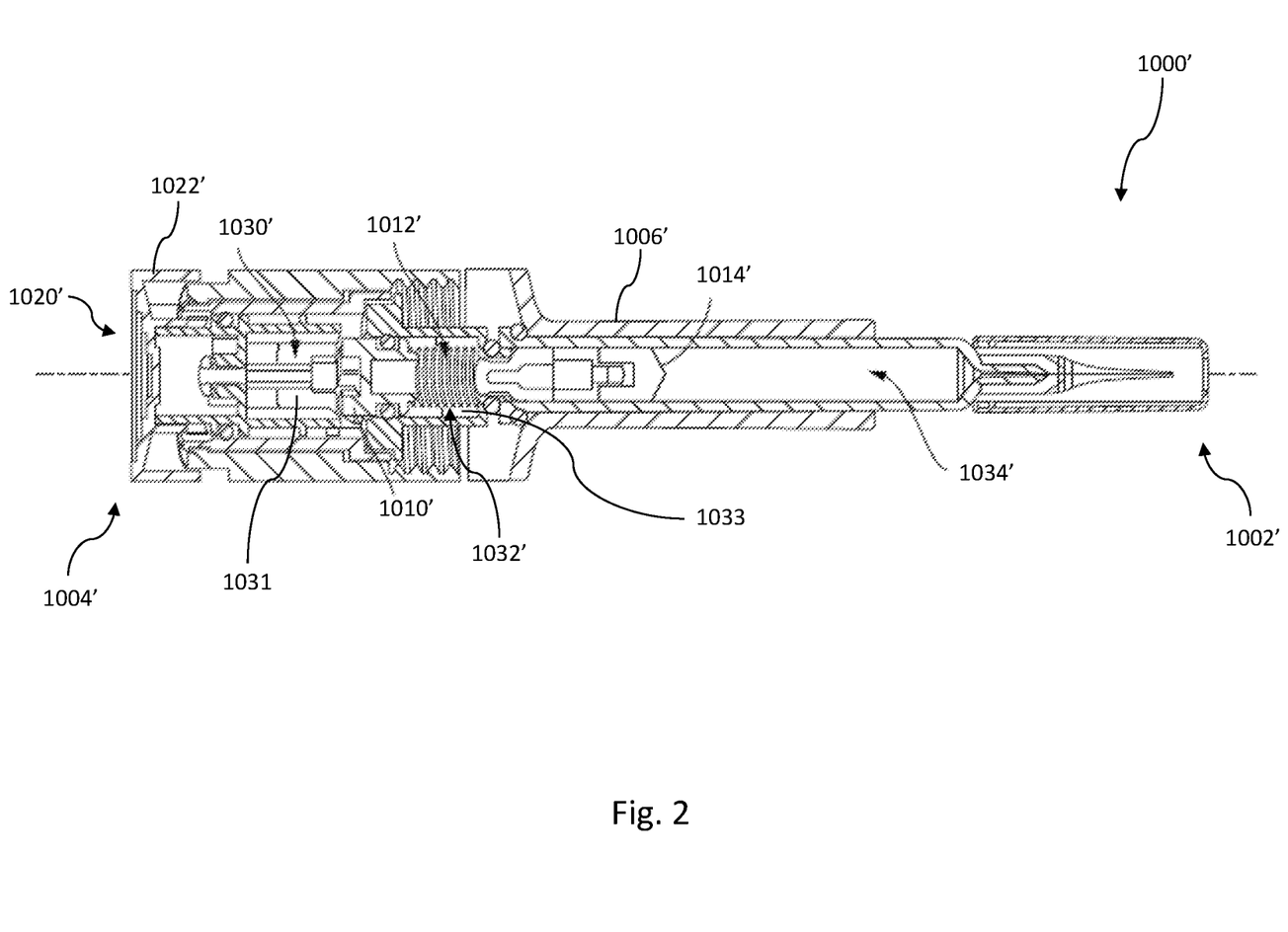
FIG. 2 shows a cross-sectional view of another exemplary delivery device of the present disclosure.

Exemplary delivery devices 1000, 1000' are shown in FIGS. 1 and 2 for delivering a therapeutic fluid to a patient. Device 1000' is similar to device 1000, with like elements indicated by a primed reference numeral. The following description refers to device 1000, but this description is also applicable to device 1000'. Other suitable delivery devices may be provided.

The illustrative device 1000 is an elongate structure that extends from a first, distal end 1002 (illustratively, a lower end) to a second, proximal end 1004 (illustratively, an upper end). The illustrative device 1000 includes a substantially cylindrical barrel or housing 1006 containing a piston 1010, a spring 1012, and a plunger 1014. At first end 1002, device 1000 includes a patient delivery mechanism (not shown), such as a syringe or a needle, for example. At second end 1004, device 1000 includes an actuator assembly 1020.

Initially, device 1000 may be provided in a loaded configuration in which piston 1010 is held downward in barrel 1006 to compress spring 1012, as shown in FIG. 1. In this loaded configuration, barrel 1006 of device 1000 may be divided into multiple chambers, illustratively a first actuation chamber 1030, a second reaction chamber 1032, and a third therapeutic fluid chamber 1034. The first actuation chamber 1030 is located above piston 1010 and contains a first reagent 1031 (FIG. 2). The second reaction chamber 1032 is located below piston 1010 and contains a second reagent 1033 (FIG. 2). The third therapeutic fluid chamber 1034 is located below plunger 1014 and contains the therapeutic fluid (not shown). In the illustrative embodiment, these three chambers 1030, 1032, and 1034 are coaxial, and each is depicted as having a cylindrical shape. Device 1000 may be stored in this loaded configuration.

When device 1000 is ready for use, device 1000 may be moved to an unloaded or delivery configuration to deliver the therapeutic fluid to the patient. This step may involve pressing a button 1022 of actuator assembly 1020 downward relative to barrel 1006. In the illustrated device 1000, the downward movement of button 1022 causes piston 1010 to rotate and frees piston 1010 for upward movement as spring 1012 expands from its compressed state (FIG. 1) to its neutral or released state.

The upward movement of piston 1010 causes actuation chamber 1030 to communicate with reaction chamber 1032. The first reagent from actuation chamber 1030 is exposed to the second reagent in reaction chamber 1032, and this exposure leads to a gas-generating chemical reaction inside device 1000. The generated gas causes the pressure in device 1000 to increase, which pushes plunger 1014 downward and forces the therapeutic fluid out of therapeutic fluid chamber 1034 and into the patient.

Additional details regarding device 1000, device 1000', other suitable devices, and suitable reagents, chemical formulations, and reactions used to operate such devices are further described in the following references, the disclosures of which are expressly incorporated herein by reference in their entirety: U.S. Pat. No. 9,321,581, filed Oct. 15, 2013, and titled "Process and Device for Delivery of Fluid by Chemical Reaction"; U.S. patent application Ser. No. 14/434,586 (U.S. Publication No. 2015/0314070), filed Oct. 15, 2013, and titled "Chemical Engines and Methods for Their Use, Especially in the Injection of Highly Viscous Fluids"; and International (PCT) Application No. PCT/US2018/017547, filed Feb. 9, 2018, and titled "Processes and Devices for Delivery of Fluid by Chemical Reaction".

3. CONTROLLED GAS-GENERATING CHEMICAL REACTIONS

There are many suitable chemical reagents that can be used within the drug delivery devices of the present disclosure to generate a gas. Examples of generated gases include carbon dioxide gas, nitrogen gas, oxygen gas, chlorine gas, etc. Desirably, the generated gas is inert and non-flammable. The amount of gas needed to operate the drug delivery device and the desired rate of delivery for the therapeutic fluid may impact the type, amount, phase, and concentration of each reagent used in the device.

According to an exemplary embodiment of the present disclosure, the first reagent is a liquid reagent and the second reagent is a polymer reagent. In one particular embodiment, the liquid reagent is a liquid base and the polymer reagent is a polymeric acid. As shown in Example 1 below, such liquid base-polymeric acid reactions may proceed at a slower and more linear rate than traditional non-polymer based reactions, for example. This liquid base-polymeric acid combination uses the diffusion properties of the polymer to control the rate of the reaction and thus the production of gas and delivery rate of the therapeutic fluid.

Returning to the illustrated device 1000 of FIG. 1, the liquid reagent may be contained in the first actuation chamber 1030, and the polymer reagent may be contained in the second reaction chamber 1032. When the device 1000 is actuated, the liquid reagent may travel from the first actuation chamber 1030, past the freed piston 1010, and into contact with the polymer reagent in the second reaction chamber 1032 to undergo a liquid base-polymeric acid gas-generating reaction.

Examples of suitable liquid bases include sodium bicarbonate, potassium bicarbonate, and potassium carbonate. Other ingredients may also be present along with the bicarbonates, such as diatomaceous earth solid particles. In various embodiments, the liquid base may be a solid dissolved in a solvent or solvent and non-solvent (e.g., water) mixture, while in other embodiments, the liquid base is in a liquid phase. In addition, the liquid base may be insoluble in alcohols (i.e., potassium bicarbonate). The liquid base may also comprise a solid base and a liquid solvent that are initially separate in a loaded configuration of the device and combined in response to an actuation of the device.

In various embodiments, the polymeric acid may be formed as a powder, a dry absorbent polymer matrix formed in various ways, or a gel. For example, the polymeric acid of the present disclosure may be prepared by performing a gel polymerization process. This process may involve mixing one or more liquid acids (which may also be referred to herein as "primary" liquid acids), a desired amount of water, one or more photoinitiators, and one or more cross-linkers, if applicable. Examples of suitable liquid acids include acrylic acid, methacrylic acid, malleic acid, and combinations thereof. The acid solution can then be formed into various shapes and cured with UV light for a period of time. The UV light drives the polymerization and cross-linking reactions to form polyacrylic acid (PAA) gel, polymethacrylic acid (PMAA) gel, polymalleic acid gel, or combinations thereof. For example, 14 millimeter gel discs may be prepared with an acid solution made of liquid acid, 0.5% of a photoinitiator (e.g., methylpropiophenon), and 5000 parts per million of a cross-linker (e.g., acrylamide, ethylene glycol) that is drawn into a syringe with a 30-gauge needle and injected between two glass plates through rubber o-rings to form discs, which are then UV cured for one minute. A dry absorbent polymer matrix may be formed in numerous ways, including, for example, compression molding, injection molding, electrospinning, and film casting.

In forming the polymeric acid, the water content of the acid solution, curing conditions, pH of the acid solution, and other variables may be adjusted to change properties of the polymeric acid. In one particular embodiment of a chemical reaction system of the present disclosure, PAA gel is the polymeric acid and potassium bicarbonate is the liquid base. These reagents may react to produce carbon dioxide gas. In operation, when the liquid base comes into contact with the polymeric acid gel, the base diffuses into the free volume of the polymeric acid gel, reacts with new acidic moieties, and generates gas. The reaction is complete when the liquid base has fully diffused, reacted, and equilibrated within the polymeric acid gel. The free volume (e.g., cavities, etc.) within the polymeric acid in gel form may be modified to alter the diffusion of the base into the gel and therefore the reaction between the reactants and gas production.

In general, the polymeric acid may be the limiting reactant in the chemical reaction systems of the present disclosure. In an exemplary embodiment, if an excess amount of the polymeric acid is present in the system, such an excess amount may be 7 mol. % or more. This excess amount will increase the available surface area for the chemical reaction and decrease dead volume in the system, which would increase the rate and quantity of gas generated by the system.

As shown in the Examples below, the rate and quantity of gas generated by the liquid base-polymeric acid reaction within the chemical reaction system may be adjusted in a plurality of ways. As a general rule of thumb, the higher the surface area-to-volume ratio, the acid concentration, and/or the cross-linking of the polymeric acid, and the faster the reaction and the production of gas that is used to propel the chemical reaction system, and therefore the faster the delivery of the therapeutic fluid.

The surface area-to-volume ratio of the chemical reaction system can be controlled in a variety of ways to adjust the rate and quantity of gas generated. For example, changing the shape and/or form of the polymeric acid to increase its surface area (i.e., making thin sheets of the polymeric acid in gel form, pelletizing the polymeric acid, or electrospinning the polymeric acid into fibers) may increase the reaction rate and delivery rate. In the fiber embodiment, the presence of the fibers themselves may also improve wettability of the acid or the tendency of one fluid to spread on, or adhere to, a surface of the acid through capillary wetting. The size and arrangement of the fibers themselves may be controlled during the electrospinning process, such as by using a relatively large target electrode to produce straight and loosely-packed fibers or a relatively small target electrode to produce curled and densely-packed fibers.

Additionally, the concentration/water content of the acid in the chemical reaction system is controllable to adjust the rate and quantity of gas generated. For example, higher quantities of the primary acid used to form the polymeric acid may be added, other secondary acids, for example citric acid, may be present along with the polymeric acid, and/or the water content of the primary acid may be reduced to increase the acid concentration and therefore increase the reaction rate of the reagents within the chemical reaction system. In some embodiments, the secondary acids or other ingredients do not necessarily chemically bond to the polymeric acid or the base reagents, but rather may either be applied to the surface of the polymeric acid matrix or gel or mixed within the polymeric acid form. In embodiments where the secondary acid sits on the surface of the polymeric acid, the liquid base may quickly reach and react with the secondary acid for an initial pressure boost. By contrast, in embodiments where the secondary acid is embedded in the cavities of the polymeric acid, the reaction between the liquid base and the secondary acid may be delayed and prolonged for an extended pressure boost. In general, the higher the acid concentration or the lower the water content, the faster the reaction of the chemical reaction system, and thus the faster the delivery rate of the therapeutic fluid from the drug delivery device (see FIG. 7). Similarly, the lower the acid concentration or the higher the water content, the slower the reaction of the chemical reaction system, and thus the slower the delivery rate of the therapeutic fluid from the drug delivery device.

Furthermore, in various embodiments, the polymeric acid reagent may be cross linked to adjust the rate and quantity of gas generated within the chemical reaction system. Cross-linking reduces the solubility of the polymeric acid (e.g., fibers) in the aqueous reaction mixture allowing the polymeric acid to retain it form, swell like a sponge and increase the surface area of contact rather than dissolving and collapsing. The physical swelling of the polymeric acid may also contribute to the pressure increase in the drug delivery device. Thus, cross-linking the polymeric acid produces a faster reaction rate of the reagents, and thus a faster the delivery rate of the therapeutic fluid. In addition, by heating the fibers during cross-linking, moisture is dried off the fibers of the polymeric acid allowing the dry fibers to take up the aqueous reaction mixture more quickly and completely, thus increasing the delivery rate even more.

4. EXAMPLES

Example 1: Liquid-Polymer Reaction Vs. Liquid-Powder (Non-Polymer) Reaction

In this Example, the inventors evaluated the generated pressure and reaction rate in a drug delivery device (expressed as pressure (psig) vs. time (s)) and the resulting therapeutic delivery or flow rate of a therapeutic fluid (expressed as mass (g) vs. time (s)) having a viscosity of about 20 cP at a temperature of about 20° C.

Figure 3:
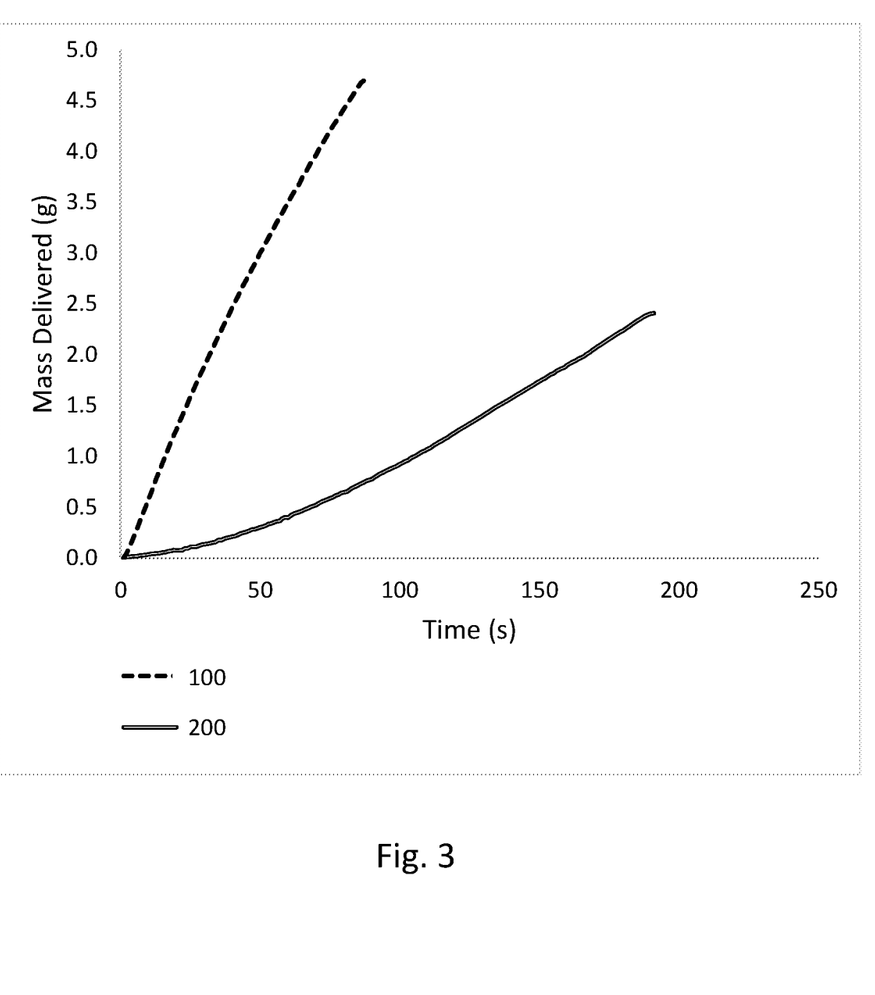
FIG. 3 shows a graphical comparison between a reaction rate of a liquid base and a polymeric acid of a chemical reaction system of the present disclosure and a reaction rate of a powder base and liquid non-polymeric acid of a chemical reaction system of the prior art.
Figure 4:
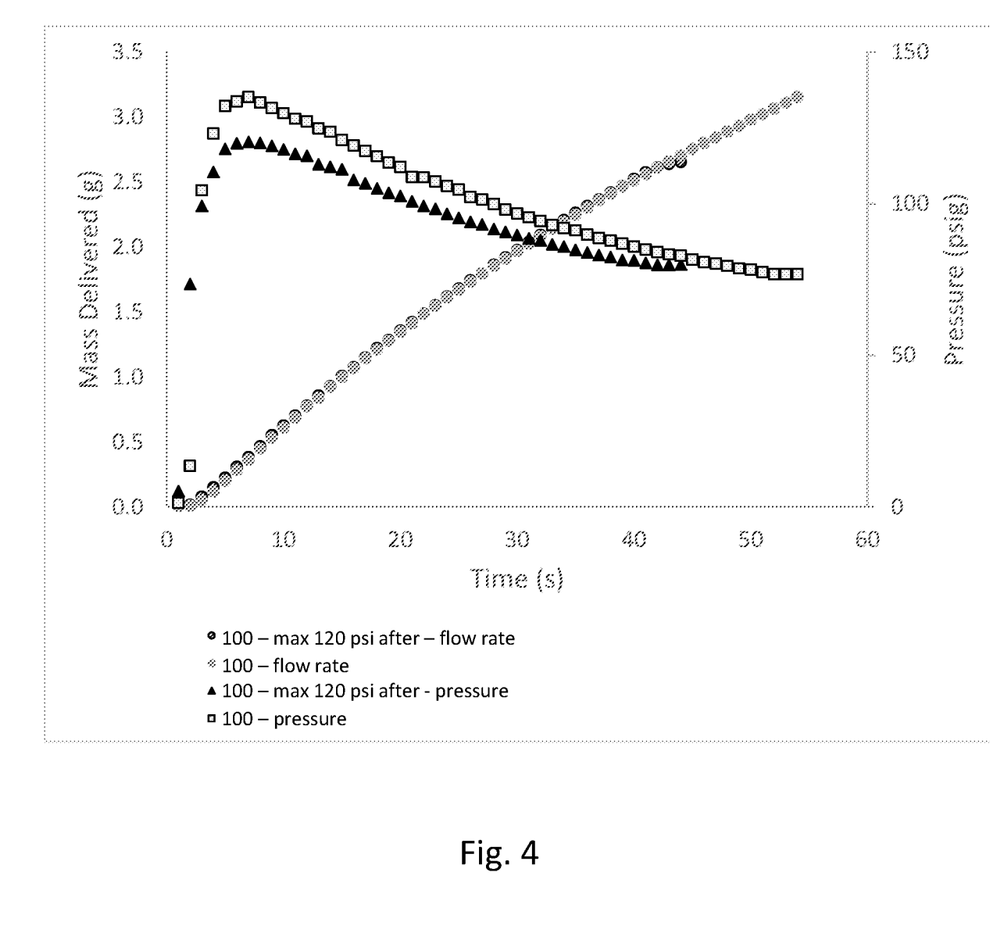
FIG. 4 shows a graphical representation of a pressure and a delivery/flow rate of a powder base and liquid non-polymeric acid of a chemical reaction system of the prior art.

With reference to FIGS. 3 and 4, it is demonstrated that the reaction rate between the liquid base and the polymeric acid in the liquid-polymer based reaction 200 was a controlled quasi-linear one that is slower, more linear than the traditional non-polymer based reactions 100. More specifically, FIGS. 3 and 4 demonstrate that the mass delivered of reaction system 200, which included a reaction between 2.11 grams of 100% PAA in 4 pieces and 0.84 milliliters of liquid saturated potassium bicarbonate, increased in a controlled linear fashion. By contrast, sharper, drastic increases in the mass delivered and the pressure were exhibited by reaction system 100, which included a reaction between 286 mg potassium bicarbonate dry powder and 550 µL citric acid liquid (1.6M) for delivering the same therapeutic fluid.

Example 2: Acid Concentration/Water Content

Figure 5:
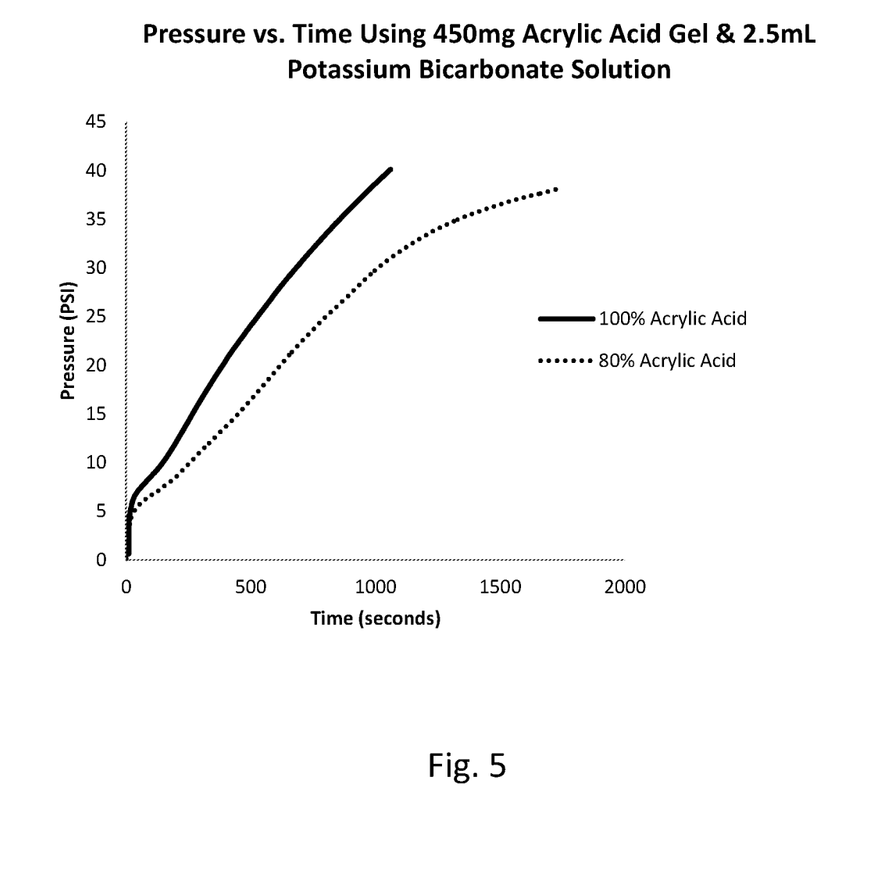
FIG. 5 shows a graphical comparison of reaction rates of two exemplary reactions of the present disclosure adjusted by controlling water content/acid concentration.

Two separate variations of the gel discs of the polymeric acid were prepared. One variation included 100% acrylic acid, while the other variation included 80% acrylic acid. The gel discs, having 14 millimeter diameters, were prepared by mixing liquid acrylic acid, 0.5 wt. % of methylpropiophenone, and 5000 parts per million of acrylamide, drawing the solution into a syringe with a 30-gauge needle, injecting the solution between two glass plates through rubber o-rings, and then curing the formed discs with UV light for approximately one minute. Additionally, a liquid solution of dissolved potassium bicarbonate was prepared to a concentration of 25 mg/mL. Three 150 mg acrylic acid gel discs totaling 450 mg were placed in a pressure vessel, which was subsequently closed and connected to a pressure sensor. Then, 2.5 mL of the potassium bicarbonate solution was injected into the pressure vessel and data was read from the pressure sensor. As shown in FIG. 5, the rate of pressure generation is impacted by the acidic concentration or water content of the polymeric acid. More specifically, as shown, the lower acid concentration or higher water content (80% acrylic acid) generated gas at a slower rate than the higher acid concentration or lower water content (100% acrylic acid).

Example 3: Variations of the Chemical Reaction System and Reaction/Delivery Rates In this Example, the inventors evaluated the generated pressure rate in a drug delivery device (expressed as pressure (psig) vs. time (s)) and the resulting therapeutic delivery rate of a therapeutic fluid (expressed as mass (g) vs. time (s)) having a viscosity of about 20 cP at a temperature of about 20° C. (density of 1.17 g/mL).

Figure 6:
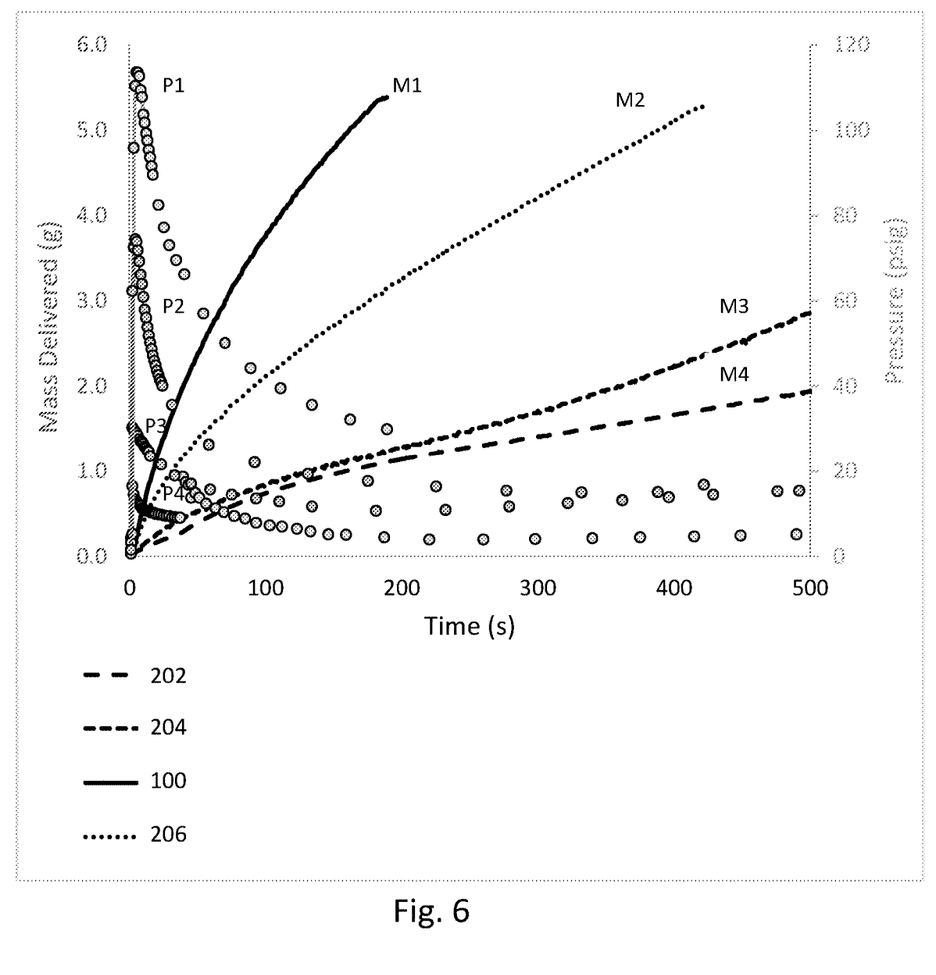
FIG. 6 shows a graphical representation of reaction and delivery/flow rates of chemical reaction systems of the present disclosure adjusted by control of various aspects of the chemical reaction systems.

FIG. 6 shows delivery rates of four different reaction systems. Reaction system 100 (M1/P1) is a comparative prior art reaction system including a reaction between 0.1 grams of powder potassium bicarbonate and 0.55 milliliters of liquid 1.6M citric acid. Reaction system 202 (M4/P4) is a reaction system of the present disclosure including a reaction between 0.186 grams of 100% PAA gel and 0.84 milliliters of liquid saturated potassium bicarbonate (at room temperature). Reaction system 204 (M3/P3) is a reaction system of the present disclosure including a reaction between 0.190 grams of 100% PAA gel provided in 16 different pieces (increased surface area-to-volume ratio) and 0.84 milliliters of liquid saturated potassium bicarbonate. Reaction system 206 (M2/P2) is a reaction system of the present disclosure including a reaction between 0.196 grams of 100% PAA gel provided in pieces (increased surface area-to-volume ratio), 0.025 grams of citric acid (increased acid concentration) and 1.0 milliliters of liquid saturated potassium bicarbonate. As shown in FIG. 6, prior art reaction system 100 has a faster rate than reaction systems 202, 204, and 206 of the present disclosure, and reaction system 206 of the present disclosure, which has a higher acid concentration and higher surface area-to-volume ratio, has a faster delivery rate than reaction system 204, which only has an increased surface area-to-volume ratio, and reaction system 202, which has neither. In addition, reaction system 204, which only has an increased surface area-to-volume ratio, is shown to have a faster delivery rate than reaction 202 which has neither.

Figure 7:
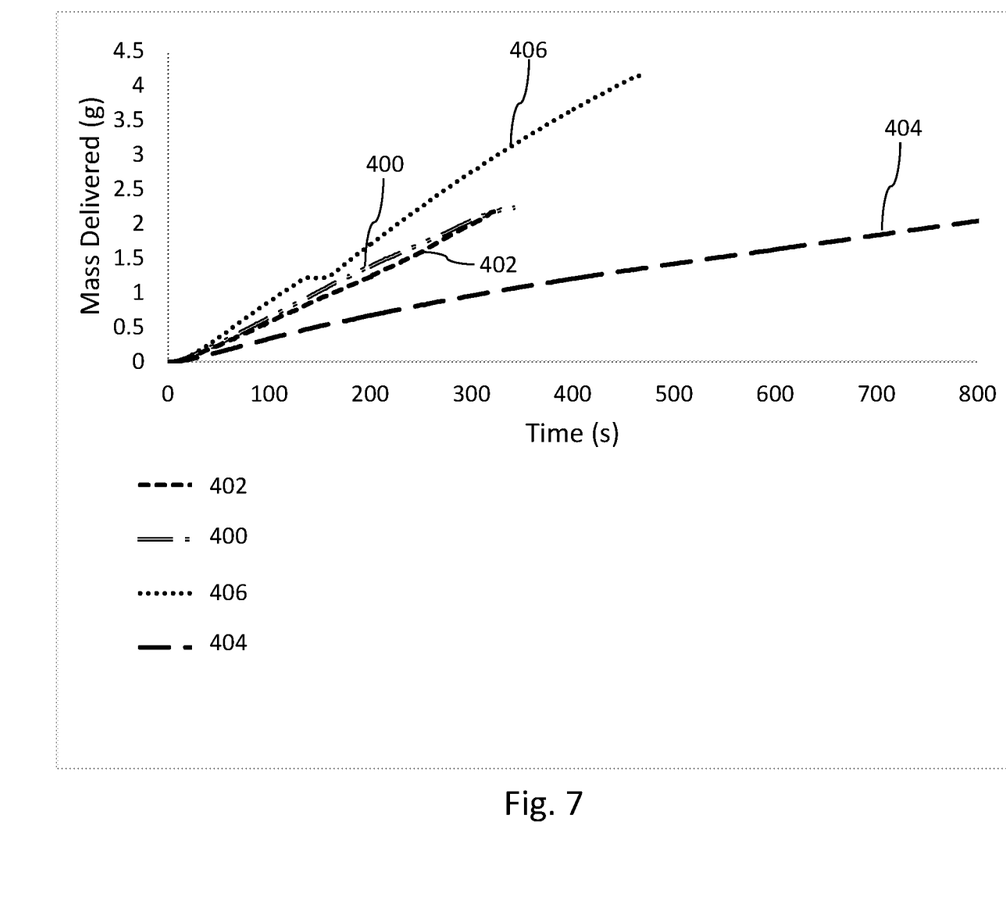
FIG. 7 shows a graphical representation of delivery/flow rates of chemical reaction systems of the present disclosure adjusted by varying acid content of the chemical reaction systems.

FIG. 7 shows delivery rates of various reaction systems of the present disclosure with various adjustments to acid content. Reaction system 400 included a reaction between 0.200 grams of 100% PAA gel formed as fiber material pieces (increased surface area-to-volume ratio) and 0.84 milliliters of liquid saturated potassium bicarbonate. Reaction system 402 included a reaction between 0.413 grams of 100% PAA gel (increased acid content with additional polymeric acid) formed as electrospun fiber material pieces (increased surface area-to-volume ratio) and 0.84 milliliters of liquid saturated potassium bicarbonate. Reaction system 404 included a reaction between 0.193 grams of 100% PAA gel formed as electrospun fiber material pieces (increased surface area-to-volume ratio) with 20% (w/w %) citric acid (increased acid content with secondary acid) and 0.84 milliliters of liquid saturated potassium bicarbonate. Reaction system 406 included a reaction between 0.423 grams of 100% PAA gel with 14% (w/w %) citric acid (increased acid content with additional polymeric acid and a secondary acid) and 0.84 milliliters of liquid saturated potassium bicarbonate. As shown in FIG. 7, reaction system 406, which has increased acid content with additional polymeric acid and a secondary acid, has a faster delivery rate than reaction systems 400, 402, and 404, which only have increased acid content due to either additional polymeric acid or the addition of a secondary acid. In addition, reaction system 402, which has increased acid content of the polymeric acid, and reaction system 400 which has increased acid content of the polymeric acid as compared to reaction system 404, have faster delivery rates than reaction system 404, which has increased acid content only by the inclusion of a secondary acid. Without wishing to be bound by theory, the faster delivery rates of reaction system 406 over reaction systems 400 and 402 may be attributed to the additional polymeric acid in addition to the addition of a secondary acid, and the faster delivery rates of reaction system 400 and 402 over reaction system 404 may be attributed to the increase of acid content provided by additional polymeric acid as opposed to a secondary acid. Thus, in general, a reaction system of the present disclosure with additional polymeric acid and the addition of a secondary acid will have a faster delivery rate than a reaction system with the additional polymeric acid or the addition of a secondary acid, and a reaction system with additional polymeric acid will have a faster delivery rate than a reaction system with the addition of a secondary acid.

Figure 8:
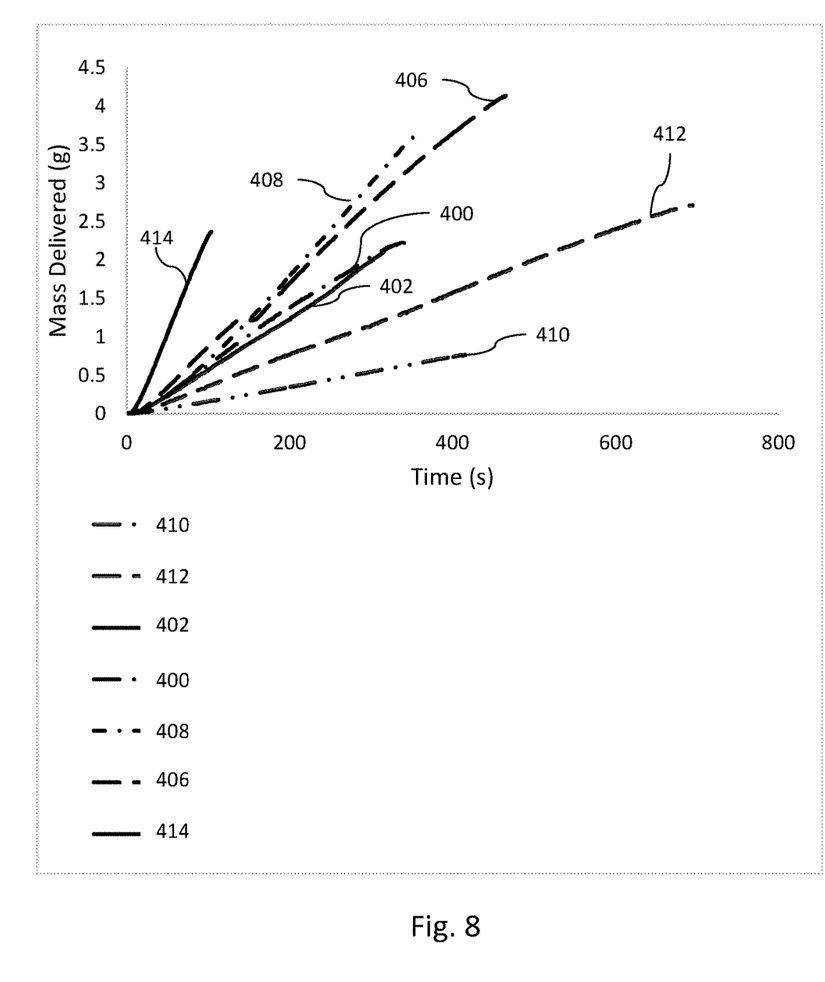
FIG. 8 shows a graphical comparison of delivery/flow rates of chemical reaction systems of the present disclosure that are cross-linked versus reaction rates of chemical reaction systems of the present disclosure that are non-cross-linked.

FIG. 8 shows delivery rates of reaction systems 400, 402, and 406, further compared to the delivery rate of reaction systems 408, 410, 412, and 414 of the present disclosure. Reaction system 408 included a reaction between 0.228 grams of cross-linked 100% PAA gel with 14% (w/w %) citric acid (increased acid content due to a secondary acid and cross-linking), and 0.84 milliliters of liquid saturated potassium bicarbonate. Reaction system 410 included a reaction between 0.150 grams of 100% PAA gel with 14% (w/w %) citric acid (increased acid content due to a secondary acid) and 0.84 milliliters of liquid saturated potassium bicarbonate. Reaction system 412 included a reaction between 0.162 grams of 100% PAA gel with 14% (w/w %) citric acid (increased acid concentration) and 0.84 milliliters of liquid saturated potassium bicarbonate. Reaction system 414 included a reaction between 0.200 grams of 100% PAA gel formed as fiber material pieces (increased surface area-to-volume ratio) which is cross-linked with ethylene glycol (with cross-linking) and 0.84 milliliters of liquid saturated potassium bicarbonate. As shown in FIG. 8, reaction systems 414 and 408, which have cross-linked polymeric acid matrices, have delivery rates that are faster than that of each of reaction systems 400, 402, 404, 406, 410, and 412. Without wishing to be bound by theory, the slower delivery rates of reaction systems 400, 402, 404, 406, 410, and 412 may be attributed to the non-cross linked polymer chains which likely dissolved rapidly.

Figure 9:
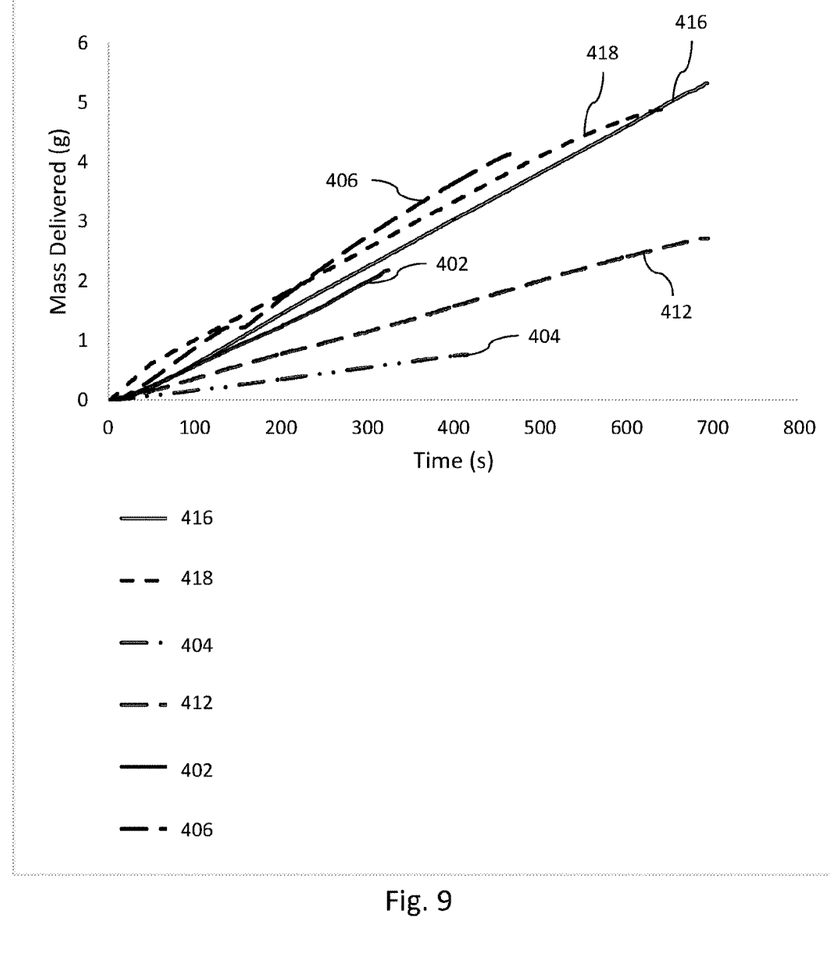
FIG. 9 shows a graphical representation of delivery/flow rates of chemical reaction systems of the present disclosures adjusted by varying surface area to volume ratios of the chemical reaction systems.

FIG. 9 shows delivery rates of reaction systems 402, 404, 406, and 412 further compared to the delivery rate of reaction systems 416 and 418 of the present disclosure. Reaction system 416 included a reaction between 0.203 grams of 100% PAA gel with citric acid (increased acid concentration) and 0.84 milliliters of liquid saturated potassium bicarbonate. Reaction system 418 included a reaction between 0.203 grams of 100% PAA gel with citric acid (increased acid concentration) and 0.84 milliliters of liquid saturated potassium bicarbonate. As shown in FIG. 9, reaction system 406, which has increased acid content of polymeric acid and a secondary acid, has a faster delivery rate than that of each of reaction systems 418, 416, 402, 412, and 404. In addition, reaction systems 418 and 416, which have increase surface area to volume ratios, have faster delivery rates than that of reaction systems 402, 412, and 404. Furthermore, reaction systems 402 and 412, which have higher acid contents of the polymeric acid than reaction system 404, have faster delivery rates than reaction system 404. As such, in general, higher acid content caused by both increased amounts of the polymeric acid and the addition of a secondary acid have increased delivery rates over reaction systems with higher surface area-to-volume ratios which have increased delivery rates over reaction systems with increased acid content caused by only one of an increase in amount of the polymeric acid and the addition of a secondary acid.

Figure 10:
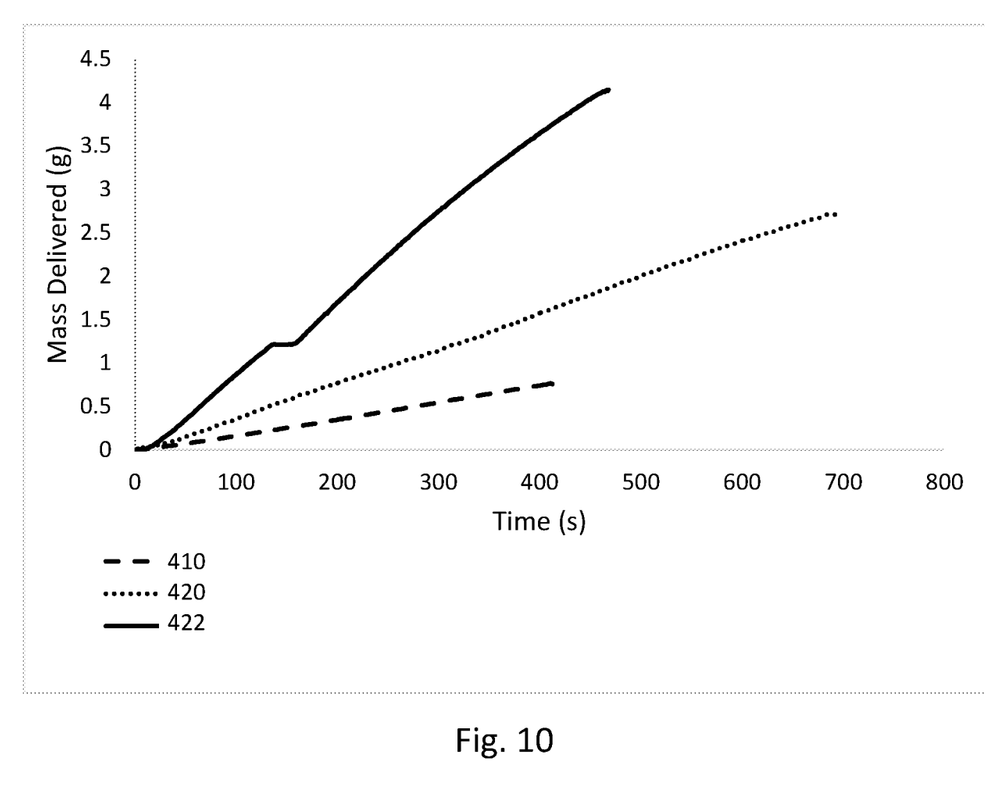
FIG. 10 shows a graphical representation of delivery/flow rates of chemical reaction systems of the present disclosures adjusted by controlling weight of a polymeric acid of the chemical reaction systems.

FIG. 10 shows the effect of varying acid concentrations on the delivery rate of chemical reaction systems of the present disclosure. Reaction system 422 included a reaction between 0.423 grams of 100% PAA gel with 14% (w/w %) citric acid and 0.84 milliliters of liquid saturated potassium bicarbonate. Reaction system 420 included a reaction between 0.162 grams of 100% PAA gel with 14% (w/w %) citric acid and 0.84 milliliters of liquid saturated potassium bicarbonate. As shown in FIG. 10, the delivery rate of reaction system 422 (highest acid content of polymeric acid) is faster than that of reaction system 420, which is faster than that of reaction system 410 (lowest acid content of polymeric acid). Thus, the delivery rate of the reaction system, in general, increases as the acid content of the polymeric acid in the reaction system increases, and decreases as the acid content of the polymeric acid decreases, since the acid is the limiting reactant. In general, if enough acid is present within the system to react with all, or nearly all, of the liquid base, the delivery rate of the system is estimated to deliver 5 mL of the therapeutic agent between approximately 9 and 15 minutes.

Figure 11:
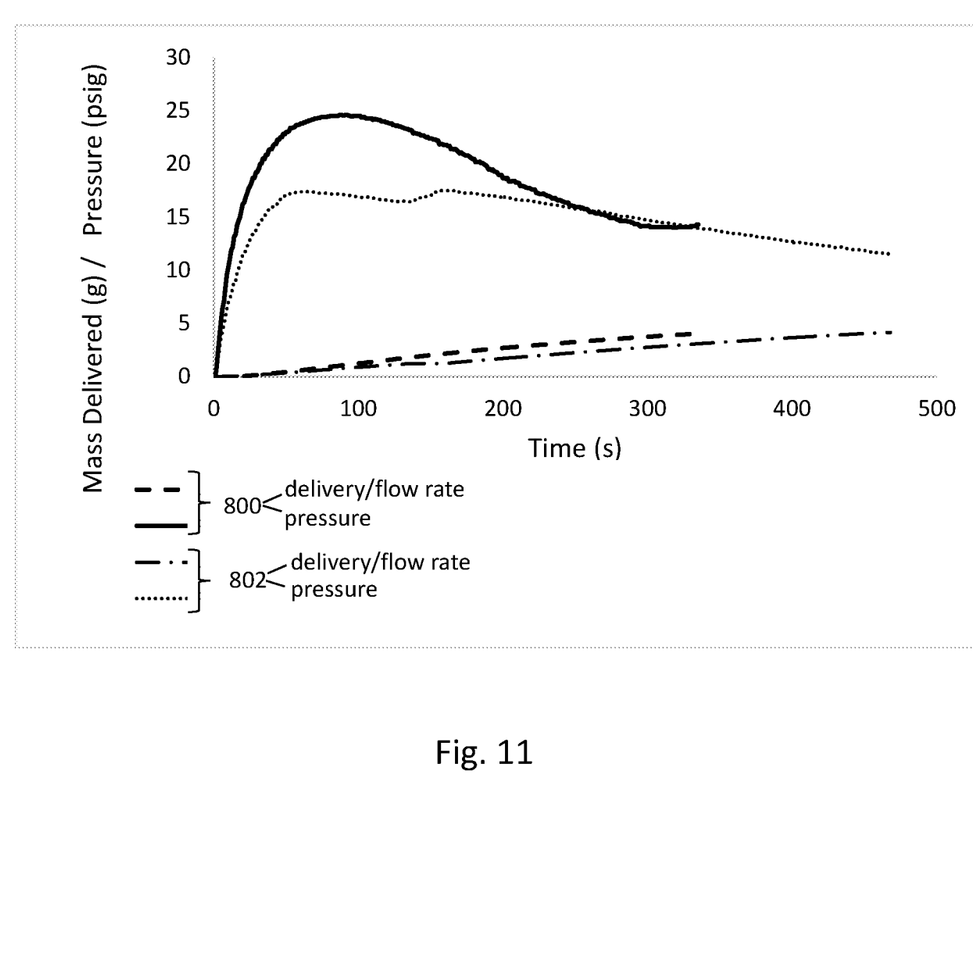
FIG. 11 shows a graphical representation of reaction rates and delivery/flow rates of chemical reaction systems of the present disclosure adjusted by controlling surface area characteristics of the polymeric acid of the chemical reaction systems.

FIG. 11 shows a comparison between delivery rates and pressures of a reaction system with cross-linked gel 800 and a reaction system without cross-linked gel 802. Reaction system 800 included a reaction between 0.418 grams of 100% PAA gel with citric acid which was cross-linked and 0.84 milliliters of liquid saturated potassium bicarbonate, and reaction system 802 included a reaction between 0.423 grams of 100% PAA gel with 19% (w/w %) citric acid which was not cross-linked and 0.84 milliliters of liquid saturated potassium bicarbonate. As shown in FIG. 11, reaction system 800, which included the cross-linked gel, had a faster delivery rate and a higher pressure than reaction system 802, which did not include cross-linked gel.

Figure 12:
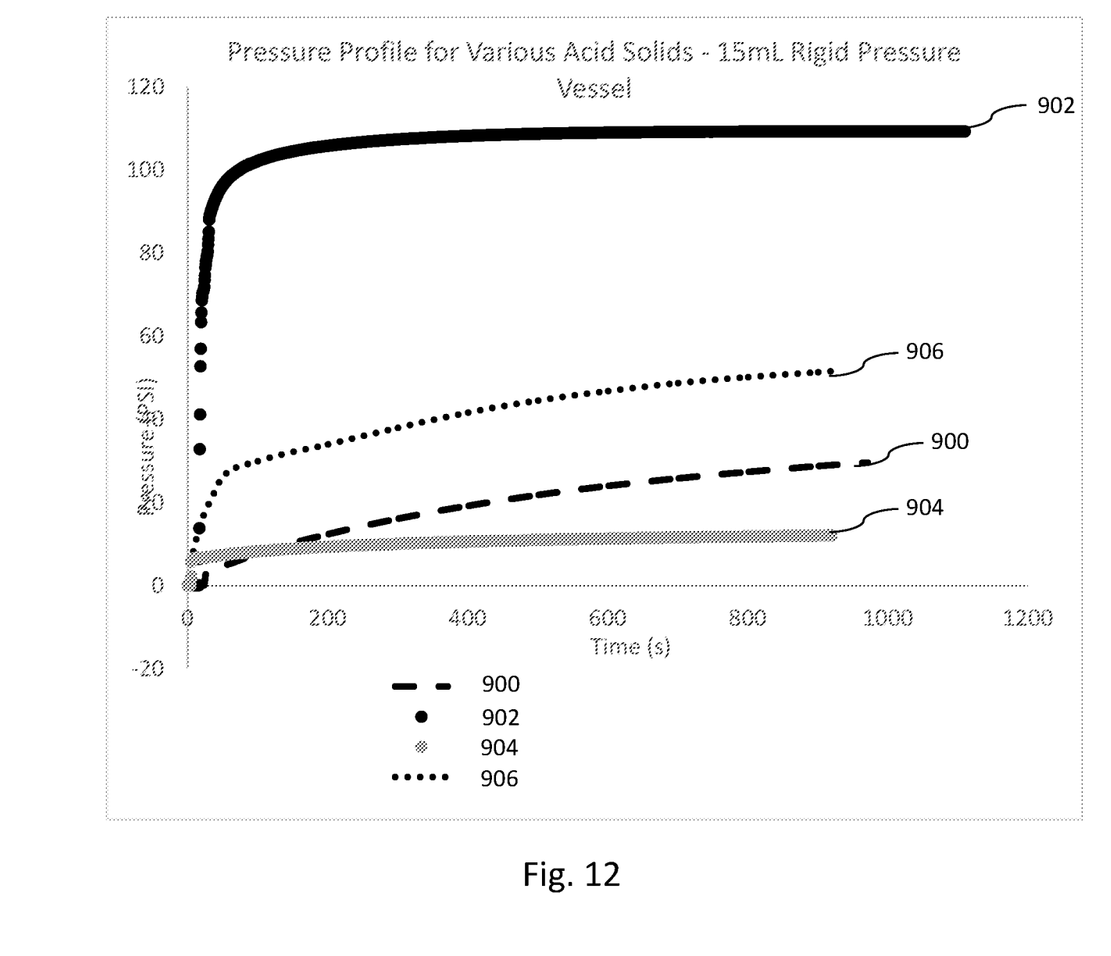
FIG. 12 shows a graphical comparison of pressures profiles of various chemical reaction systems of the present disclosure having various physical forms of a polymeric acid and a chemical reaction system using citric acid powder.

FIG. 12 shows a graphical comparison of pressures and flow/delivery rates of various chemical reaction systems of the present disclosure and prior art having various physical forms of the acid. More specifically, FIG. 12 shows the variation in pressure profiles when using a loose powder form of the prior art acid (citric acid) versus a loose powder form of a polymeric acid of the present disclosure versus a compressed tablet of a polymeric acid of the present disclosure. Reaction system 900 included a PAA tablet weighing 0.510 grams, reaction system 902 included 0.410 grams of citric acid powder, reaction system 904 included 0.414 grams of PAA powder with a particle size of 450,000 MV (mean diameter in microns), and reaction system 906 included 0.425 grams of PAA powder with a particle size of 1,000 MV (mean diameter in microns). As shown in FIG. 12, reaction system 902 including the citric acid powder has a higher pressure profile than both the PAA tablet and powder of reaction systems 900, 904, and 906, and the PAA powder with the smaller particle size (1000 MV) of reaction system 906 has a higher pressure profile than the PAA tablet of reaction system 900 and the PAA powder with the larger particle size (450,000 MV) of reaction system 904.

In total, the reaction rate, the pressure generation rate, and the resulting therapeutic delivery rate of the chemical reaction system of the present disclosure can be controlled across a wide range. As such, the delivery rate of the therapeutic fluid from the drug delivery device can also be controlled across a wide range. With reference to FIGS. 6-9, for example, the reaction rate of the chemical reaction system may increase with the various adjustments in the following order: polymeric acid alone, polymeric acid with increased surface area-to-volume ratio and increased acid concentration, polymeric acid with increased surface area-to-volume ratio, polymeric acid with increased acid concentration, polymeric acid with increased acid concentration and cross-linked, and polymeric acid with increased surface area-to-volume ratio and cross-linked.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for delivering a therapeutic fluid by a chemical reaction, the device comprising:
a housing having a first chamber, a second chamber separated from and downstream of the first chamber, and a third chamber separated from the first and second chambers;
wherein the device has:
a loaded configuration in which the first chamber is separated from the second chamber and contains a liquid base, the second chamber contains a polymeric acid and a secondary acid, and the third chamber contains the therapeutic fluid, wherein the polymeric acid is formed as at least one of a gel and a dry polymeric matrix, and the secondary acid is located on a surface of the polymeric acid; and
a delivery configuration in which the first chamber is in communication with the second chamber and the liquid base travels from the first chamber into the second chamber and reacts with the polymeric acid to generate a propellant gas that delivers the therapeutic fluid from the third chamber.

2. The device of claim 1, wherein the liquid base is a carbonate-containing base.

3. The device of claim 2, wherein the carbonate-containing base is at least one of sodium bicarbonate, potassium bicarbonate, and potassium carbonate.

4. The device of claim 1, wherein the polymeric acid is cross-linked.

5. The device of claim 1, wherein the polymeric acid includes at least one of polyacrylic acid, polymethacrylic acid, and polymalleic acid.

6. The device of claim 1, wherein the polymeric acid has an acid content of 80% or more.

7. The device of claim 6, wherein the polymeric acid has an acid content of 100%.

8. The device of claim 1, wherein the polymeric acid is formed as a gel, and the secondary acid is located on the surface of the polymeric acid gel and embedded in cavities of the polymeric acid gel.

9. The device of claim 1, wherein the secondary acid is citric acid.

10. The device of claim 1, wherein the polymeric acid is cross-linked and formed as a plurality of fibers that are heated during cross-linking to remove moisture from the fibers.

11. The device of claim 1, wherein the polymeric acid is in the form of a disc.

12. The device of claim 1, wherein the polymeric acid is formed as a gel, the gel being formed from a plurality of electrospun fibers.

13. The device of claim 1, wherein the housing is elongated and the first, second, and third chambers are coaxial, and the device further includes a needle at a first end of the housing in communication with the third chamber and an actuator assembly at a second end of the housing for actuating the device.

14. The device of claim 1, wherein the device further comprises a piston positioned in the housing between the first and second chambers, the second chamber is separated from the first chamber by the piston in the loaded configuration, and in the delivery configuration the piston moves to place the first chamber in communication with the second chamber to expose the polymeric acid to the liquid base.

15. The device of claim 14, wherein the device further comprises a plunger positioned in the housing, the third chamber is separated from the second chamber by the plunger, and the plunger pushes the therapeutic fluid from the third chamber in the delivery configuration.

* * * * *